Oct. 4, 1949. S. B. ROBERTS Plant Pat. 877
ROSE PLANT
Filed July 24, 1947
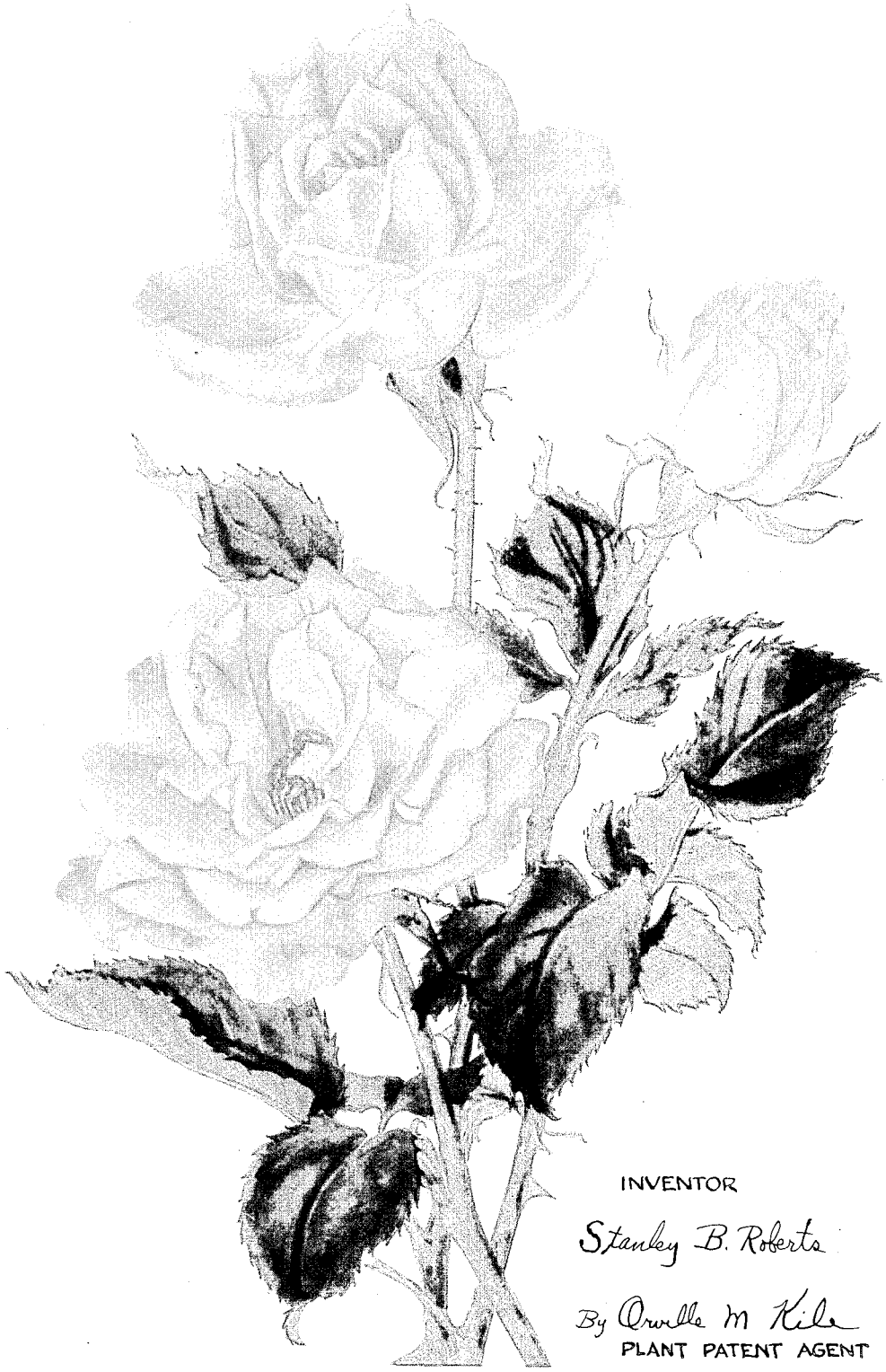
INVENTOR
Stanley B. Roberts
By Orville M Kile
PLANT PATENT AGENT Patented Oct. 4, 1949

Plant Pat. 877

UNITED STATES PATENT OFFICE

877

ROSE PLANT

Stanley B. Roberts, Westport, Conn.

Application July 24, 1947, Serial No. 763,391

1 Claim. (Cl. 47—61)

My present invention pertains to a new and distinct variety of rose plant of the hybrid tea class. It does particularly well as an outdoor rose but can also be used as a greenhouse forcing rose.

The new variety originated as the result of a cross made by me at my Madison, N. J., greenhouses, between Golden Rapture as the female parent and Queen Mary as the male parent. Although appearing to be of the Talisman type, especially in the early stages of flower opening, its parentage does not include Talisman, and important differences are found both in the plant itself and in the flower produced by it. It has been asexually reproduced through several seasons and its characteristics appear to be permanent.

Accompanying illustrations show three specimens of the flower of this new variety in the various stages of opening, together with portions of stems and foliage—all in approximately their true colors in the original paintings.

A detailed description of the plant and flower follows, in which color plate references indicate Ridgway's Color Standards and Nomenclature.

*The plant*

Growth habits: Very strong vigorous bush.

Blooming habit: Continuous bloomer, producing a large number of good flowers throughout the season.

Stems: Not exceedingly heavy but very strong. Only medium in length. Color between Parrot Green and Grass Green (Plate VI). Many light colored, downward-pointing thorns are found irregularly spaced upon the stem.

Foliage: Compound, with 3 to 7 leaflets.

*Quantity.*—Abundant.

*Size.*—Medium, terminal leaflet measuring approximately 2¼ inches by 1⅝ inches.

*Shape.*—Leaflets oval, with pointed apex which often has sidewise curve.

*Color.*—Medium green, approximately Deep Dull Yellow Green (1) (Plate XXXII) on the upper surface, and Bice Green (Plate XVII) on under surface.

*Texture.*—Very leathery.

*Rachis.*—Medium heavy; short. Upper side grooved; under side has occasional thorns.

*Stipules.*—Medium length; narrow with long points turning out abruptly.

*The flower*

Bud:

*Size.*—Medium.

*Form.*—Long-pointed, with conspicuous neck. Later becomes ovoid and much like the Talisman bud.

*Color.*—Outer edge and veinings are approximately Peach Red (Plate I). Large aiglet of Deep Chrome (Plate III) suffuses into the Peach Red.

*Sepals.*—Short and relatively simple, with only a few small branches on the sides. Reflex early.

*Peduncle.*—Short, bringing foliage near flower. Strong and capable of holding flower perfectly erect. Covered with fine prickles.

Bloom:

*Size.*—Medium, measuring about 4 inches across when fully open.

*Form.*—At first typically Talisman cup-shape with petals imbricated. Later the petals reflex in triangular shape and the flower has a spiked effect.

*Petalage.*—Usual number of petals is about 40 to 45.

*Fragrance.*—Pronounced and lasting.

*Lasting quality.*—Flower opens rapidly but lasts exceedingly well after opening.

*Color.*—The color of the flower is pretty evenly spread. At first this color is between Jasper Red (Plate XIII) and Rose Doree (Plate I) in tone but very much more brilliant. Later the color is somewhat lighter, the nearest color in Ridgway's at that stage being Peach Red (Plate I) with the central petals more nearly Strawberry Pink (Plate I). When the rose is fully open and the petals reflexed, the total color effect is Geranium Pink to Rose Doree (Plate I), varying a little with different specimens. Under surface of the flower petals is much the same color as the bud. The inside color of the petals is always brilliant in the open flower as contrasted with the bronzy color of the open Talisman which it resembles in some respects.

Petals:

*Texture.*—Heavy and leathery.

*Shape.*—Almost round with fluted point at top.

*Size.*—Large.

*Behavior.*—Clinging until old.

Reproductive organs:

*Pistils.*—Many; bunched in center. *Stigmas*—large; dull yellow. *Styles*—very dark red, approaching purple.

*Stamens.*—Many, surrounding bunched pistils. *Filaments*—light yellow; slender and of uneven lengths. *Anthers*—large, dark yellow.

Having thus disclosed my invention, I claim:

The new and distinct variety of hybrid tea rose plant of the general Talisman type, substantially as herein disclosed, characterized particularly by its very strong stems; the greater petalage of its blooms; and the distinctive bright color of its blooms which differs considerably in various stages of opening but which falls in the range between Rose Doree and Jasper Red.

STANLEY B. ROBERTS.

No references cited.